March 6, 1973 T. YUKAWA Plant Pat. 3,316
CARNATION PLANT
Filed July 19, 1971
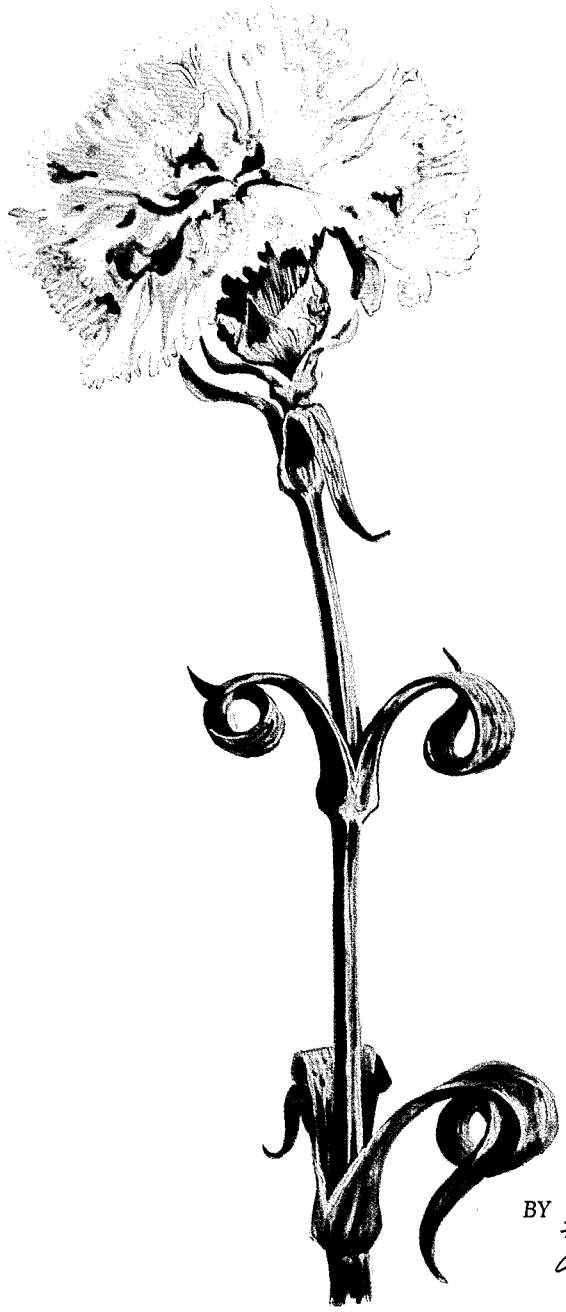
INVENTOR.
TERUO YUKAWA
BY Flehr, Hohbach, Test, Albritton & Herbert
ATTORNEYS United States Patent Office Plant Pat. 3,316
Patented Mar. 6, 1973

3,316
CARNATION PLANT

Teruo Yukawa, 1913 Hackett Ave.,
Mountain View, Calif. 94040

Filed July 19, 1971, Ser. No. 134,830
Int. Cl. A01h 5/00
U.S. Cl. Plt.—73 1 Claim This invention relates to a carnation plant and more particularly a new carnation plant having a red flower and foliage of unique character.

This new carnation is from an unnamed sport which has a color of red closest to the red carnation plant Scania 3C. The parentage of this unnamed sport is Elliott's Improved White Sim (unpatented) registered with the American Carnation Society on Feb. 17, 1954. The parent of the latter is the William Sim Carnation described in U.S. Plant Patent No. 669 issued on Jan. 15, 1946.

Since the color break was first observed, many hundreds of cuttings have been planted and grown.

Asexual reproduction of the newly discovered carnation plant was made at Mountain View, Calif. by taking cuttings in the years 1968 through 1970 and growing them. Cuttings so taken and grown have consistently produced flowers with blossoms of the red color and with foliage much thicker, heavier and huskier than that of its parent, the Improved White Sim plant, or the Scania 3C.

In the drawing there is illustrated a blossom of the new carnation plant in full bloom and showing a typical stock and other foliage characterizing the plant, varying color values of red being employed to depict better the appearance of the flower.

The following is a detailed description of the new carnation plant.

The description of the carnation plant in U.S. Plant Patent No. 669 and the description of Elliott's Improved White Sim carnation plant are applicable to the newly discovered variety with the exception that the newly discovered variety has a red blossom, a huskier, thicker and heavier stem and foliage, a higher crown in the blossom with from 5 to 7 fewer petals than the parent Improved White Sim and an earlier blooming than the Improved White Sim.

The petals of the flower are generally similar in size and shape to those of the parent, Improved White Sim, but are larger than the petals of the Scania 3C. The color of the petals is a uniform deep red in the major portion of the petal with a tapered white base near the flower calyx. The red color is deeper than the color of the Scania 3C. The closest descriptive term for the color of the flower is cherry red 10B8 pertaining to the brightness of the flower's color, but closer in hue to blood red identified 10C8 in the Reinhold Color Atlas by A. Kornerup and J. H. Wanscher published by Reinhold Publishing Corporation, New York, N.Y. (Library of Congress Catalogue No. 62–8756).

A valuable and important feature of this new carnation is that the flower is less subject to splitting than other red carnations, particularly the Scania 3C, and the shape of the flower results in fewer slabs, giving a greater proportion of the top grade of flower than do other red carnation plants. The petals are more resistant to refrigeration than other red carnations in that it has been observed to retain satisfactory commercial quality after 21 days of refrigeration in temperatures ranging from 45° to 50° F.

I claim:

1. The new and distinctive variety of carnation plant substantially as herein described and illustrated.

No references cited.

ROBERT E. BAGWILL, Primary Examiner